United States Patent
McKay (10) Patent No.: US 9,241,754 B2
(45) Date of Patent: Jan. 26, 2016

(54) NERVE AND SOFT TISSUE ABLATION DEVICE

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 281 days.

(21) Appl. No.: 13/834,619

(22) Filed: Mar. 15, 2013

(65) Prior Publication Data

US 2014/0276699 A1 Sep. 18, 2014

(51) Int. Cl.
*A61B 18/18* (2006.01)
*A61B 18/02* (2006.01)
*A61B 18/00* (2006.01)

(52) U.S. Cl.
CPC ........... *A61B 18/0218* (2013.01); *A61B 18/02* (2013.01); *A61B 2018/0044* (2013.01); *A61B 2018/00434* (2013.01); *A61B 2018/0293* (2013.01)

(58) Field of Classification Search
CPC .............. A61B 18/02; A61B 18/0218; A61B 2018/00434; A61B 2018/0044; A61B 2018/0293; A61B 2018/0231; A61B 2018/0262
See application file for complete search history.

(56) References Cited

U.S. PATENT DOCUMENTS

| | | |
|---|---|---|
| 5,147,355 A | 9/1992 | Friedman et al. |
| 5,334,181 A | 8/1994 | Rubinsky et al. |
| 5,520,682 A | 5/1996 | Baust et al. |
| 5,906,612 A | 5/1999 | Chinn |
| 6,032,675 A | 3/2000 | Rubinsky |
| 6,179,831 B1 | 1/2001 | Bliweis |
| 6,190,378 B1 | 2/2001 | Jarvinen |
| 6,485,422 B1 | 11/2002 | Mikus et al. |
| 6,579,287 B2 | 6/2003 | Wittenberger et al. |
| 6,672,095 B1 | 1/2004 | Luo |
| 6,761,715 B2 | 7/2004 | Carroll |
| 6,789,545 B2 | 9/2004 | Littrup et al. |
| 6,796,979 B2 | 9/2004 | Lentz |
| 6,902,547 B2 | 6/2005 | Aves et al. |
| 6,926,711 B2 | 8/2005 | Lentz et al. |
| 7,381,208 B2 | 6/2008 | Van Der Walt et al. |
| 7,510,554 B2 | 3/2009 | Duong et al. |
| 7,625,368 B2 | 12/2009 | Schechter et al. |
| 7,641,679 B2 | 1/2010 | Joye et al. |
| 7,846,154 B2 | 12/2010 | Bliweis et al. |

(Continued)

FOREIGN PATENT DOCUMENTS

WO 2010102310 A2 9/2010

*Primary Examiner* — George Manuel
(74) *Attorney, Agent, or Firm* — Sorell Lenna & Schmidt LLP (57) ABSTRACT

Ablation devices comprising a probe or needle useful for destroying nerve and soft tissue via a minimally invasive procedure to alleviate pain are provided. The probe comprises at least two prongs spaced apart and parallel to each other. The at least two prongs each having an interior surface and an exterior surface and an internal passage disposed in the interior surface of the at least two prongs. A filament is disposed in the internal passage of the at least two prongs that has an opening configured to release a pressurized material into the interior surface of the at least two prongs so as to cool the exterior surface of the at least two prongs to a temperature configured for ablating nerve and/or soft tissue. Methods for ablating nerve and/or soft tissue utilizing the ablation devices are also provided.

20 Claims, 2 Drawing Sheets

(56) References Cited

U.S. PATENT DOCUMENTS

| | | |
|---|---|---|
| 7,938,822 B1 | 5/2011 | Berzak et al. |
| 7,967,814 B2 | 6/2011 | Levin |
| 7,967,815 B1 | 6/2011 | Berzak et al. |
| 8,083,733 B2 | 12/2011 | Toubia et al. |
| 8,162,812 B2 | 4/2012 | Shai et al. |
| 2002/0068964 A1 | 6/2002 | Dobak |
| 2004/0024391 A1* | 2/2004 | Cytron et al. ............. 606/21 |
| 2004/0049177 A1 | 3/2004 | Zvuloni et al. |
| 2005/0177215 A1 | 8/2005 | Rosenberg |
| 2005/0240239 A1 | 10/2005 | Boveja et al. |
| 2007/0156125 A1 | 7/2007 | DeLonzor |
| 2007/0191732 A1 | 8/2007 | Voegele |
| 2008/0306475 A1 | 12/2008 | Lentz et al. |
| 2009/0036823 A1 | 2/2009 | LePivert |
| 2009/0192505 A1 | 7/2009 | Askew et al. |
| 2009/0299357 A1 | 12/2009 | Zhou |
| 2010/0168739 A1 | 7/2010 | Wu et al. |
| 2010/0179527 A1 | 7/2010 | Watson et al. |
| 2010/0292764 A1 | 11/2010 | Soomro et al. |
| 2011/0270238 A1 | 11/2011 | Rizq et al. |
| 2011/0313411 A1 | 12/2011 | Anderson et al. |
| 2012/0046531 A1 | 2/2012 | Hua |
| 2012/0065630 A1 | 3/2012 | Berzak et al. |
| 2012/0089047 A1 | 4/2012 | Ryba et al. |
| 2012/0109116 A1 | 5/2012 | Asconeguy et al. |
| 2012/0253336 A1 | 10/2012 | Littrup et al. |

* cited by examiner

NERVE AND SOFT TISSUE ABLATION DEVICE

FIELD

The present invention relates generally to devices and methods for ablating a material or substance. More specifically, the devices and methods are useful for removing nerve and/or soft tissue via a minimally invasive procedure to alleviate pain.

BACKGROUND

Acute and chronic pain management has been a concern for as long as medicine has been practiced. Several methods of inducing analgesia and anesthesia have been developed. For example, the use of chemical substances is perhaps the most common approach to pain relief which requires suitable substances that are effective, safe to humans, and do not cause complications or abnormal reactions. Despite the great advances that have been made in the field of anesthesiology, and in the field of pain relief in general, there are still some drawbacks to chemical-based approaches. For instance, the anesthetics generally available today must be administered in carefully graduated doses to assure the patient's well being, require extended periods of fasting prior to treatment, and are often accompanied by undesirable after effects such as nausea.

One alternative approach that is commonly used for providing pain relief is ablation in which nerves and/or tissue is removed and/or destroyed. Two approaches to removing tissue via ablation are through cold or hot ablation procedures and techniques. Various categories of ablation include but are not limited to electrical, radiation, light, radiofrequency, ultrasound, cryotherapy, thermal, microwave and hydromechanical. One form of hot ablation is radiofrequency ablation. During radiofrequency (RF) ablation, current passing through tissue from the active electrode leads to ion agitation, which is converted by means of friction into heat. The process of cellular heating includes almost immediate and irreparable cellular damage, which leads to coagulation necrosis. Because ion agitation, and thus tissue heating, is greatest in areas of highest current density (e.g., closest to the active electrode tip), necrosis is limited to a relatively small volume of tissue surrounding the RF electrode.

Another form of ablation uses cold ablation and is called cryoablation. During cryoablation, tissue is frozen or rapid freeze/thaw cycles are inflicted upon the tissue. There are many advantages to using cryoablation instead of radiofrequency ablation. For example, cryoablation is safer especially near critical vasculature and there is less risk of post-procedure neuritis or neuromas following neuroablation for the treatment of pain. Cryoablation allows treatment mapping pre and post procedure where areas of tissue can be mapped by limited, reversible and/or freezing. Cryoablation can be monitored and visualized on ultrasonography, CT and MRI. Moreover, because nerve cooling is anesthetic, cryoablation is a less painful procedure than thermal ablation techniques.

The current procedures and techniques using cryoablation used destroy tissue due to rupturing of cells and/or cell organelles within the tissue. Deep tissue freezing is affected by insertion of a tip of a cryosurgical device into the tissue, either transperineally, endoscopically or laproscopically, and a formation of, what is known in the art as, an ice ball around the tip. During freezing, ice formation within the extracellular space creates an osmotic gradient, resulting in cellular dehydration. Ice crystals then form within the cells causing cell membranes to rupture resulting in cell death.

In addition, when the adjacent tissues are present at opposite borders with respect to the freeze treated tissue and since the growth of the ice ball is in a substantially similar rate in all directions toward its periphery, if otherwise, the ice ball reaches one of the borders before it reaches the other border, and decision making must be made on whether to continue the process of freezing, risking damage to close healthy tissues, or to halt the process of freezing, risking a non-complete destruction of the treated tissue.

Traditional cryoablation systems can provide removal capabilities of soft tissue via the application of single needles that form an ice ball centered around a tip, but may also cause a high level of collateral thermal damage. Further, these devices may suffer from an inability to control the area of necrosis in the tissue being treated. The low temperature generated by these systems causes freezing of the surrounding tissue, leading to increased pain and slower recovery of the remaining tissue. Further, the desire for a cryoablation device to provide for effective ablation of soft tissue may compromise the ability to provide consistent ablation without significant collateral damage.

Another problem with currently available cryoablation devices is that they attempt to destroy tissue by using a single probe, which generates a large ice ball that creates a larger area for ablation. As a result, there is an increase in the amount of surrounding tissue damage near the surgical site.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Accordingly, there is a need for devices and methods to provide efficient destruction of nerve and/or soft tissue by ablating a larger surface area perpendicular to the device yet minimizing tissue damage proximal and distal to the device that can be used during a minimally invasive procedure and/or during an open surgical procedure. For example, along the length of the nerve. Further, there is a need for devices and methods that provide fine ablation capabilities of nerve and/or soft tissue. Devices and methods that do not cause a high level of collateral thermal damage and allow for the control of necrosis in the tissue being treated are also needed.

SUMMARY

Ablation devices and methods are provided that allow a larger surface area of destruction of the nerve and other soft tissue in a minimally invasive procedure. The ablation devices and methods provided allow the tips of the device to be easily positioned in an optimal location to obtain improved ablation with minimal unwanted destruction to adjacent nerve and/or soft tissue.

In some embodiments, the ablation devices and methods provided allow destruction of nerves and other soft tissue via a minimally invasive procedure to alleviate pain. The ablation devices and methods disclosed comprise a probe having at least two prongs spaced apart and parallel to each other. The at least two prongs each have an interior surface and an exterior surface and an internal passage disposed in the interior surface of the at least two prongs. A filament is disposed in the internal passage of the at least two prongs having an opening configured to release a pressurized material (e.g., gas or liquid) into the interior surface of the at least two prongs so as to cool the exterior surface of the at least two prongs to a temperature configured for ablating nerve and/or soft tissue.

In some embodiments, a cryoablation device comprises a probe having at least two prongs spaced apart and parallel to each other, the at least two prongs each having an interior surface and an exterior surface; an internal passage disposed in the interior surface of the at least two prongs; a filament disposed in the internal passage of the at least two prongs, the filament having an opening configured to release a pressurized material into the interior surface of the at least two prongs so as to cool the exterior surface of the at least two prongs to a temperature configured for ablating nerve and/or soft tissue at a facet joint.

In certain embodiments, methods for destroying nerves and other soft tissue via a minimally invasive procedure to alleviate pain are also provided. Destruction of the target nerve or soft tissue can eliminate and/or reduce pain symptoms. Specific clinical applications of the disclosed ablation instrument include destruction of nerves causing facet and discogenic back and leg pain, destruction of soft tissue causing stenosis pain symptoms, and many other orthopedic and oral maxillofacial pains.

In some embodiments, methods of ablating a nerve and/or soft tissue include positioning a distal region of a probe of a cryoablation device adjacent a nerve or soft tissue to be ablated, the probe having at least two prongs spaced apart and parallel to each other, the at least two prongs each having an interior surface and an exterior surface, an internal passage disposed in the interior surface of the at least two prongs, a filament disposed in the internal passage of the at least two prongs, the filament having an opening configured to release a pressurized material into the interior surface of the at least two prongs so as to cool the exterior surface of the at least two prongs to a temperature configured for ablating nerve and/or soft tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Devices for efficient destruction and/or removing of a material or substance such as nerve and soft tissue suitable for use in open surgical and/or minimally invasive procedures for the treatment of pain are disclosed. The following description is presented to enable any person skilled in the art to make and use the present disclosure. Descriptions of specific embodiments and applications are provided only as examples and various modifications will be readily apparent to those skilled in the art.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

DEFINITIONS

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Cryoablation

Cryoablation devices have been available to surgeons to treat many medical conditions, for example, in the treatment of tumors in lung, liver, kidney and other body organs. Cryoablation has also been used for treatment of tumors, cardiac arrhythmias, chronic and post-operative pain, bone fracture and soft tissue wounds.

Cold temperatures have been used to decrease inflammation and to relieve pain since the ancient Egyptians. Liquid air and carbon dioxide were used to treat skin lesions in the beginning of the twentieth century. In 1950, liquid nitrogen was introduced into clinical practice for the cryosurgical ablation of a variety of skin diseases and allowed for deeper tissue to be treated with cryoablation. In 1961, a liquid nitrogen probe was developed and was used to treat Parkinson's disease as well as inoperable brain tumors. From 1980-2000, systems emerged based on an advanced gas expansion method known as the Joule-Thomson Principle. This principle allows for temperature change of a gas or liquid when it is forced through a valve or porous plug while being kept insulated so that no heat is exchanged with the environment. The refrigerant could be stored at room temperature and the difficulties associated with supplying liquid nitrogen to the operating room disappeared. Three main refrigerants were utilized: nitric oxide, liquid nitrogen and argon. For over 20 years, rigid cryoprobes have existed for percutaneous use or in open invasive surgical procedures. For example, cryoprobes are used for freezing a range of lesions from prostate tissue to metastatic cancers in liver. Neuronal tissue has been frozen with such devices for the relief of pain.

Current cryoablation procedures and technique employ cryoprobes that utilize single needles that form an ice ball centered around a tip. The ice ball is essentially spherical or oval in shape and the area of complete nerve ablation is only approximately half of the ice ball diameter. Therefore, to ablate a particular area the ice ball needs to be approximately twice as large resulting in unnecessary tissue damage proximal and distal to the needle tip. As one travels up the probe toward the source of pressurized liquid or gas the temperature increases. Therefore, the probe of the present disclosure focuses the about −40° C. to about −160° C. temperature at or near the tip for enhanced ablation.

The present disclosure incorporates at least two or more parallel needles into a single device that is capable of ablating over a large surface area perpendicular to the needles. The needles operate simultaneously and are positioned over a specific distance apart from each other such that the zone of complete ablation merge or overlap with each other resulting in a larger continuous perpendicular ablation area than a single needle is capable of. The present disclosure forms smaller ice balls such that less adjacent tissue damage occurs.

Figure 1:
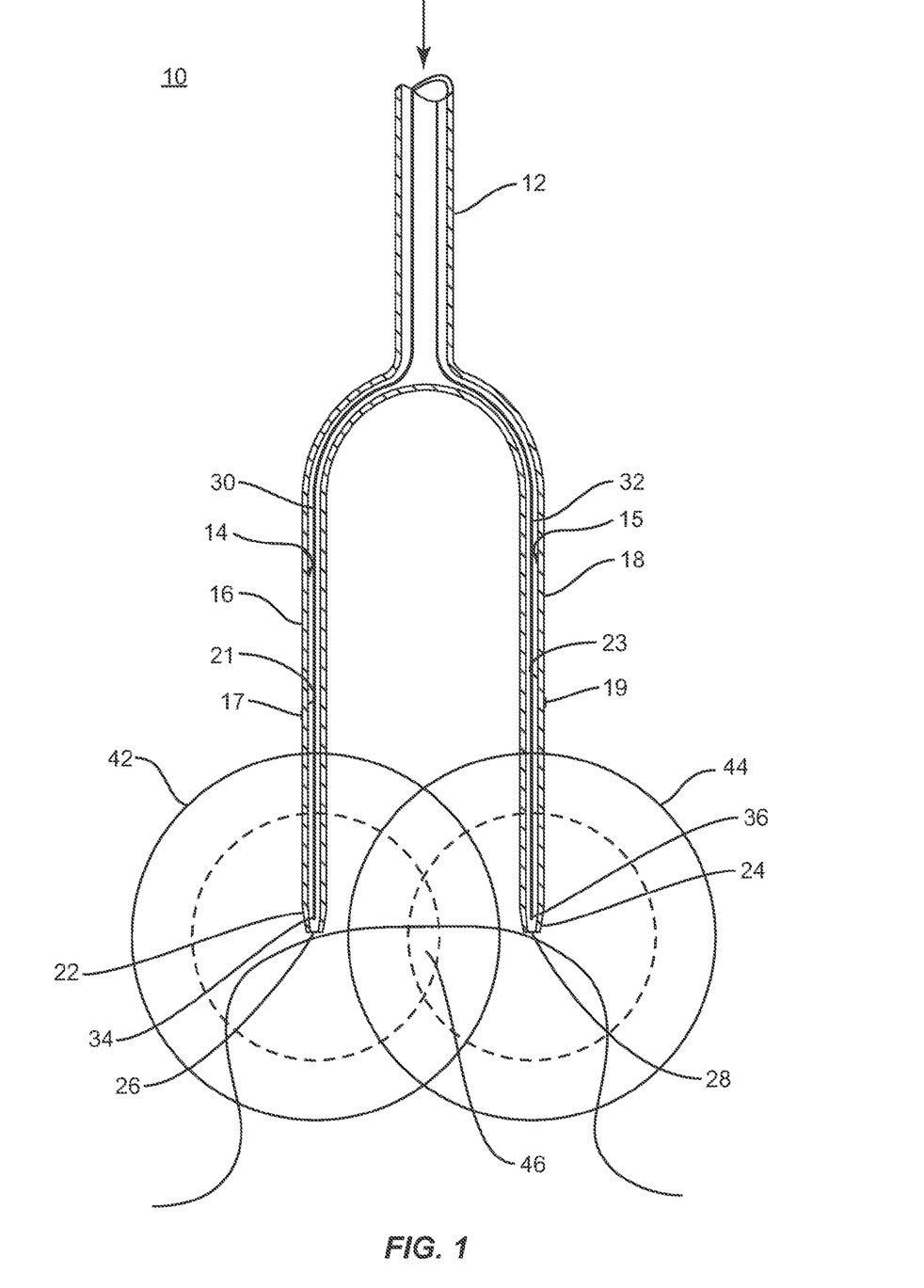
FIG. 1 illustrates a cross sectional front view of an ablation device in accordance with one embodiment of the present disclosure.

As illustrated in FIG. 1, the present ablation device 10 comprises a probe 12. The dimensions of the probe, among other things, will depend on the site that needs ablation. For example, the width of the epidural space is only about 3-5 mm for the thoracic region and about 5-7 mm for the lumbar region. Thus, the probe, in various embodiments, can be designed for these specific areas.

Some examples of lengths of the probe, may include, but are not limited to, from about 50 to 150 mm in length, for example, about 65 mm for epidural pediatric use, about 85 mm for a standard adult and about 110 mm for an obese adult patient. The thickness of the probe will also depend on the site of that needs ablation. In various embodiments, the thickness includes, but is not limited to, from about 0.05 to about 1.655. The probe may be the widest or smallest diameter or a diameter in between for insertion into a human or animal body. The widest diameter is typically about 14 gauge, while the smallest diameter is about 25 gauge. In various embodiments the probe can be about 18 to about 22 gauge.

Probe 12 includes at least two prongs, such as, for example, a first prong 16 and a second prong 18. Prongs 16, 18 are needles that are spaced apart and are parallel to each other. Prongs 16, 18 are spaced about at about a distance of 0.5 cm. In some embodiments, prongs 16, 18 are spaced apart at about 0.2 to about 0.4 cm. In some embodiments, prongs 16, 18 are spaced apart at about 0.6 to about 0.8 cm. Prongs 16, 18 each have an interior surface 14, 15 and an exterior surface 17, 19. Prongs 16, 18 each include an internal passage 21, 23 disposed in the interior surfaces 14, 15 of prongs 16, 18 respectively. In some embodiments, prongs 16, 18 can have one or more passages in each prong for pressurized material to be released into the prong as well as recirculation throughout the prong. Exterior surface 17 of prong 16 comprises a tip 22 and exterior surface 19 of prong 18 comprises a tip 24 positioned at a distal end of the probe. Tips 22, 24 are pointed to allow for easy pushing through tissues and include openings 26, 28 respectively.

In some embodiments, the tips of the prongs can be round or tapered. In various embodiments, the tips are smooth for insertion. In some embodiments, the probe 12 has a blunt tip such that the surgeon or health practitioner can eliminate any difficulty in positioning the probe tip in the optimal location to get an optimal and consistent clinical result. The use of probe 12 results in avoiding necrosis of adjacent tissue, which can lead to clinical adverse events that requires the tissue to undergo excessive repair itself after the procedure. In some embodiments, positioning of the tips 22, 24 allows ablation to be applied near the tips and avoids hemisphere spacing around the tips to avoid unwanted necrosis.

In some embodiments, a lubricant is provided to assist in the insertion of tips 22, 24 within the nerve and/or soft tissue. In some embodiments, the lubricant can be, without limitation, polyethylene glycol (PEG), hyaluronic acid, hyaluronan, lubricin, polyethylene glycol, and any combinations thereof.

In various embodiments, prongs 16, 18 are about 20 gauge. In some embodiments, prongs 16, 18 are about from 14 gauge to about 25 gauge. In some embodiments the prongs can be increasing and or decreasing in thickness throughout the prongs. In some embodiments, the prongs may be tapered and/or angled.

Prongs 16, 18 each comprise a filament 30, 32 disposed within internal passages 21, 23 of prongs 16, 18 respectively. Filaments 30, 32 are about 0.016 inches in diameter. In some embodiments, the filaments are about 0.010 to 0.015 or about 0.17 to about 0.25 inches in diameter. The filaments are conduits for cooling and expansion of the pressurized material that is released and passed into prongs 16, 18.

Filaments 30, 32 each include an opening 34, 36 configured to release a pressurized material into interior surfaces 14, 15 of the at least two prongs. The openings may be shaped as a regular or irregular polygon including arcuate, round, square, oblong, kidney shaped, crescent, or beveled shaped. The pressurized material is released into passages 21, 23 and enters into interior surfaces 14, 15, cooling and expanding within the interior surfaces via the filaments. The material is pressurized and in some embodiments, the pressure is from about 3,000 to about 6,000 pounds per square inch (PSI).

In some embodiments, the material is in the form of argon, liquid nitrogen, nitric oxide, helium, air, krypton, carbon dioxide, tetrafluoromethane or xenon. When a high pressure material such as argon is used, argon will expand within the interior and will liquefy so as to form a cryogenic pool at the tips, cooling the surfaces of the tips. The temperature of the material is coldest at the tips of probes 16, 18. In one embodiment, tips 22, 24 are made of a heat conducting material such as metal so as to enable the formation of the ice balls. The ice balls are spherical or oval in shape.

After a period of time, ice balls 42, 44 form when the exterior surfaces at the tips 22, 24 contact nerve and/or soft tissue and when the temperature at the tips decreases from about −40° C. to about −160° C. The temperature at the surface of the ice balls is 0° C. The temperature declines exponentially towards a cool center where it reaches about −170° C. The ice balls will be formed at about 2 to about 8 minutes after the material has been released into probe 12. The spheres create a zone of complete ablation (about −20° C.) typically located within each ice ball at approximately half way between the center of the ball and its outer surface. At least a portion of ice ball 42 comes into contact and/or overlaps with ice ball 44 and the overlapped area 46 along with the ice balls creates a larger continuous perpendicular ablation area than that of a single ice ball. Prongs 22, 24 create smaller ice balls, reducing the amount of damage caused to adjacent tissue. In various embodiments, nerve and or soft tissue is completely ablated in about 3 to about 16 minutes. In various embodiments, nerve and or soft tissue is completely ablated in about 3 to about 9 minutes.

The temperature for cryoablation of the device can be selected by the user and can vary as needed. For example, the temperature that can be selected can be from −180°, −170°, −160°–150° C., −140° C., −130° C., −120° C., −110° C., −100° C., −50° C., −40° C., −3° C., −2° C., −1° C., −5° C. or to about 0° C. or any temperature in between these numbers.

In some embodiments, a heated material can pass through the internal passages of the prongs to heat the pressurized material thereby increasing temperature.

The sizes of the tips of the prongs determine the sizes of the ice balls formed. In some embodiments, the diameter of the tips are about 0.5 to about 2 mm for smaller ice balls and from about 3 to about 6 mm for larger ice balls.

Figure 2:
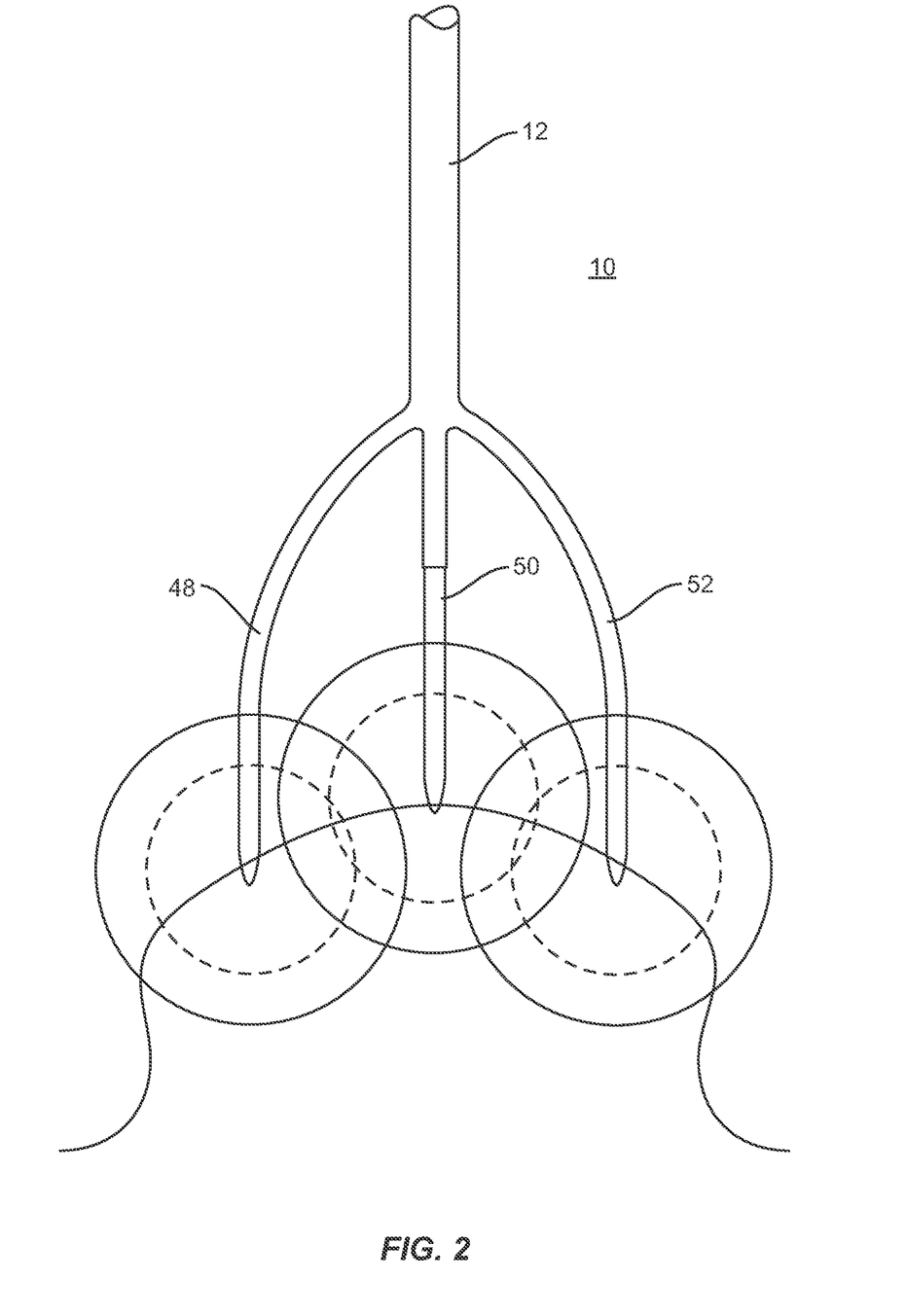
FIG. 2 illustrates a front view an ablation device in accordance with one embodiment of the present disclosure.

In one embodiment, probe 12 comprises a plurality of prongs, such as, for example, a first prong 48, a second prong 50 and a third prong 52. Prongs 48, 50 and 52 comprise tips that form an arcuate configuration to match a particular geometry to be ablated. For example, in some embodiments, prongs 48 and 52 are longer than prong 50, such that when positioned with a facet of a vertebra, the facet geometry is matched with the tips of prongs 48, 50 and 52 and the prongs are in closer proximity to the overlying nerve fibers that require smaller ice balls for nerve ablation. In various embodiments, the prongs are configured to match other anatomical tissue shapes to treat other painful conditions. In certain embodiments, each prong may be introduced at a specific depth to locally provide treatment to a portion of the surgical site while avoiding damage to other areas that are not intended to be ablated.

In various embodiments, prong 50 comprises a telescopic configuration. Prong 50 can be manually or electronically movable so as to place prong 50 into a particular position within a surgical site. In certain embodiments, all or some of the prongs comprise a telescopic configuration. In some embodiments, prong 50 is a navigational tool used to guide probe 12 into a surgical site.

In some embodiments, the prongs each comprise indicia, for example a depth indicator that may include an analog, such as, for example, a dial with a numerical indicator of angle and/or digital display, such as, for example, LED and/or LCD. The graduations may represent various indicia, such as, for example, numerical, alphabetic and/or specific conditions/orientations, such as, initial depth and/or final depth of penetration into the nerve and/or tissue.

In certain embodiments, probe 12 may include switches for manually controlling the operation of probe 12 by a medical practitioner. The switches can provide functions such as on/off, cooling, and predetermined cycles of heating and cooling by selectively and controllably communicating probe 12 with an external material container.

In some embodiments, different monitors of temperature, gas pressure and location on the probe 12 can be attached to probe 12. In some embodiments, thermal sensors may be used for measuring the temperature of the material and/or the tips of the prongs. In some embodiments, probe 12 can be operatively connected to semi-steerable or navigational sources for easier guidance into tissues. In various embodiments, the navigational sources can be coupled with a pre-procedure such as for example, CT, MRI, PET scan, etc. so that the target nerve or soft tissue to be ablated can be identified and accurately located during the procedure.

In some embodiments, probe 12 is attached to a pressure source that is configured to supply the pressurized material described above. In some embodiments, without limitation, the pressure source can be a pump, a cannula and or a catheter.

In various embodiment, at a proximal end, probe 12 can be operatively connected to a vacuum (not shown) for providing suction to ablated nerve and/or tissue. The vacuum may be used to transmit vacuum from a vacuum source (not shown) to a receiving aperture (not shown) connected to probe 12. Any suitable aspirator, cylindrical or otherwise, or other mechanism that creates vacuum upon the movement of an actuating member thereof, may be utilized as a vacuum source. The vacuum can be in communication with the tips of probe 12 for providing suction to remove ablated nerve and/or soft tissue.

With further reference to FIG. 1, not shown is an overall glass or other insulating layer covering most of the structure. In some embodiments, the coating or insulating layer can be glass or ceramic having a thickness from about 0.005 to about 0.5 mm thick or from about 0.01 to about 0.2 mm thick.

The glass type insulation is typically applied by a conventional process of dipping each relevant component prior to assembly in liquid (molten) glass and then annealing the glass. In some embodiments, the coating or insulation layer does not cover the entire probe. In some embodiments, the coating or insulation layer does cover the entire probe.

Suitable material for probe 12 can be for example, polyurethane, polyurea, polyether(amide), PEBA, thermoplastic elastomeric olefin, copolyester, and styrenic thermoplastic elastomer, steel, aluminum, stainless steel, titanium, nitinol, tungsten, molybdenum, metal alloys with high non-ferrous metal content and a low relative proportion of iron, carbon fiber, glass fiber, plastics, ceramics or a combination thereof.

In various embodiments, the probe may include radiographic markers to help indicate position on imaging procedures (e.g., CT scan, X-ray, fluoroscopy, PET scan, etc.). These may be disposed on or a portion of the probe or the prongs and include, but are not limited to, barium, calcium phosphate, and/or metal beads.

In some embodiments, probe 12 can also have blunt prong tips. As a result, the surgeon or health practitioner can eliminate any difficulty in positioning the probe tips in the optimal location to get an optimal and consistent clinical result. The use of probe 12 also results in avoiding necrosis of adjacent tissue, which can lead to clinical adverse events and requires these adjacent tissues to have to repair themselves. Positioning of the tips allows cryoablation to be applied near the tips and avoids hemisphere spacing around the tips to avoid unwanted necrosis.

In some embodiments, the tips of the prongs can comprise grooves (not shown). Grooves can have edges shaped as a regular or irregular polygon including arcuate, round, square, oblong, oval, kidney shaped, beveled, or crescent shaped. The grooves can also include ridges or have no ridges. In various embodiments, the grooves are located at the tips of the prongs and can be closed when probe 12 is inactive as probe 12 is inserted towards the desired location. Once the nerve or soft tissue to destroy is reached, grooves open, the material becomes activated to ablate the nerve or tissue protruding into each groove as probe 12 is manually pushed into it.

In certain embodiments, probe 12 can be provided with a tube or small channel (not shown) configured to deliver at the location of the severed nerve and/or soft tissue cement or polymer which can provide a physical barrier to prevent the temporary or permanent re-growth of nerve and/or soft tissue so that the pain symptoms do not return. This channel can be adjacent to the filaments in the prongs and can run parallel to the filaments such that the device can ablate and deliver a therapeutic material or barrier (e.g., polymer, cement, gel, etc.) to the area after ablating it.

Methods for Ablation

The present disclosure also provides methods for destroying or removing nerve and/or soft tissue. The methods comprise positioning a distal region of the cryoablation device 10 adjacent a nerve or soft tissue to be ablated, the probe having at least two prongs spaced apart and parallel to each other, the at least two prongs each having an interior surface and an exterior surface, an internal passage disposed in the interior surface of the at least two prongs, a filament disposed in the internal passage of the at least two prongs, the filament having an opening configured to release a pressurized material into the interior surface of the at least two prongs so as to cool the exterior surface of the at least two prongs to a temperature configured for ablating nerve and/or soft tissue. The exterior surface comprises a tip for the at least two prongs; or the exterior surface contacts nerve and or soft tissue to form an ice ball configured for ablating the nerve and/or the soft tissue; wherein the ice balls form at about 2-8 minutes, wherein at least a portion of each of the ices balls overlap causing the nerve and/or soft tissue to be ablate, and wherein the temperature of the pressurized material decreases at or near the tip and wherein the pressurized material is cooled at the tip at approximately −40° C. or cooler.

In other embodiments, the methods of the present disclosure further include delivering cement and/or a polymer through a small channel, for injection at the site of the nerve and/or soft tissue destruction to provide a physically barrier at the location of the nerve destruction to prevent temporary or permanent nerve regrowth, repair and return of the pain symptoms.

The barrier material utilized can be any suitable material effective to prevent or at least substantially inhibit the migration of substances that regrow tissue. Illustratively the barrier material can comprise a biodegradable synthetic polymer, in either flowable (and potentially hardenable) or non-flowable form. Illustratively, preferred barrier materials can have a first relatively flowable state during delivery and a second relatively less flowable state after implantation. For example, the barrier material may remain in an uncured, deformable, or otherwise configurable state during introduction, and rapidly cure, become harder or solidify after being introduced. Suitable materials that may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. In some embodiments, the barrier material can be a cement.

In several embodiments, the methods disclosed herein include operatively coupling the probe to a source of navigational capability to allow easier pushing through the tissues. In various embodiments, the methods of ablation disclosed herein can include a pre-procedure step wherein the probe can be coupled to a CT or MRI machine so that the target nerve and/or soft tissue to be ablated can be identified and accurately located during the ablation procedure.

The methods for ablation described hereinabove allow complete destruction of the nerve avoiding the problems and partial effectiveness of current cryoablation and RF devices available in the art, and also allow for more complete destruction of soft tissue that is causing stenosis pain symptoms.

As described above, the methods disclosed herein allow complete destruction of the nerve avoiding the problems and partial effectiveness of current cryoablation and RF devices mentioned above, and also allow for more complete removal of soft tissue that is causing stenosis pain symptoms.

Specific clinical application of this instrument include destruction of nerves causing facet and discogenic back and leg pain, destruction of soft tissue causing stenosis pain symptoms, and many other orthopedic and oral maxillofacial pain. Many other painful conditions associated with arthroscopic, otolaryngological or spinal procedures could use the ablation devices and methods of using these ablation devices described herein.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An ablation device comprising: a single probe having at least three prongs branching from the probe such that the at least three prongs are spaced apart and parallel to each other, the at least three prongs each having an interior surface and an exterior surface; an internal passage disposed in the interior surface of the at least three prongs; a filament disposed in the internal passage of the at least three prongs, the filament having an opening configured to release a pressurized material into the interior surface of the at least three prongs so as to cool the exterior surface of the at least three prongs to a temperature for ablating nerve and/or soft tissue, wherein one of the at least three prongs is shorter in length than the other prongs and the one prong shorter in length has a telescopic configuration to increase or decrease in length relative to the other prongs.

2. An ablation device of claim 1, wherein (i) the exterior surface comprises a tip for the at least three prongs; or (ii) the exterior surface contacts nerve and/or soft tissue to form an ice ball configured for ablating the nerve and/or soft tissue.

3. An ablation device of claim 2, wherein each of the tips are pointed.

4. An ablation device of claim 2, wherein (i) each of the tips are blunt; or (ii) the filaments are about 0.016 inches in diameter and the pressurized material expands within the internal passage of the probe to cause a decrease in the temperature of the pressurized material.

5. An ablation device of claim 2, wherein the temperature of the pressurized material decreases at or near the tip.

6. An ablation device of claim 2, wherein the pressurized material is cooled at the tip at approximately −40° C.

7. An ablation device of claim 1, wherein the at least three prongs are each in the shape of a needle.

8. An ablation device of claim 1, wherein two prongs of the at least three prongs are about 20 gauge needles and wherein the probe comprises titanium, stainless steel, tungsten, molybdenum or alloys thereof.

9. An ablation device of claim 1, wherein the material comprises a liquid or gas comprising argon, liquid nitrogen, nitric oxide, helium, air, krypton, carbon dioxide, tetrafluoromethane or xenon.

10. An ablation device of claim 1, wherein the ice balls form at about 6-8 minutes and at least a portion of each of the ice balls overlap.

11. An ablation device of claim 1, wherein the device has three prongs and one of the three prongs is shorter than the other two prongs and the shorter prong is disposed between the other two prongs.

12. An ablation device of claim 1, wherein each of the prongs includes a telescopic configuration.

13. A cryoablation device comprising:
a single probe having at least three prongs branching from the probe such that the at least three prongs are spaced apart and parallel to each other, the at least three prongs each having an interior surface and an exterior surface; an internal passage disposed in the interior surface of the at least three prongs; a filament disposed in the internal passage of the at least three prongs, the filament having an opening configured to release a pressurized material into the interior surface of the at least three prongs so as to cool the exterior surface of the at least three prongs to a temperature for ablating nerve and/or soft tissue at a facet joint, wherein one of the at least three prongs is shorter in length than the other prongs and the one prong shorter in length has a telescopic configuration to increase or decrease in length relative to the other prongs.

14. A cryoablation device of claim 13, wherein (i) the exterior surface comprises a pointed tip for the at least three prongs; or (ii) the exterior surface contacts nerve and/or soft tissue at the facet joint to form an ice ball configured for ablating the nerve and/or soft tissue at the facet joint.

15. A cryoablation device of claim 14, wherein (i) each of the tips are blunt; or (ii) the filaments are about 0.016 inches in diameter and the pressurized material expands within internal passage of the probe to cause a decrease in the temperature of the pressurized material.

16. A cryoablation device of claim 14, wherein the temperature of the pressurized material decreases at or near the tip.

17. A cryoablation device of claim 14, wherein the pressurized material is cooled at the tip from about −40° C. to about 160° C.

18. A cryoablation device of claim 13, wherein the material comprises a liquid or gas comprising argon, liquid nitrogen, nitric oxide, helium, air, krypton, carbon dioxide, tetrafluoromethane or xenon.

19. A method of ablating a nerve and/or soft tissue, comprising:
positioning a distal region of a single probe of a cryoablation device adjacent a nerve or soft tissue to be ablated, the probe having at least three prongs branching from the probe such that the at least three prongs are spaced apart and parallel to each other, the at least three prongs each having an interior surface and an exterior surface, an internal passage disposed in the interior surface of the at least three prongs, a filament disposed in the internal passage of the at least three prongs, the filament having an opening configured to release a pressurized material into the interior surface of the at least three prongs so as to cool the exterior surface of the at least three prongs to a temperature configured for ablating nerve and/or soft tissue, wherein one of the at least three prongs is shorter in length than the other prongs and the one prong shorter in length has a telescopic configuration to increase or decrease in length relative to the other prongs.

20. A method of ablating a nerve and/or soft tissue of claim 19, wherein (i) the exterior surface comprises a tip for the at least three prongs; or (ii) the exterior surface contacts nerve and or soft tissue to form an ice ball configured for ablating the nerve and/or the soft tissue; wherein the ice balls form at about 2-8 minutes, wherein at least a portion of each of the ices balls come in contact and/or overlap causing the nerve and/or soft tissue to be ablated, and wherein the temperature of the pressurized material decreases at or near the tip and wherein the pressurized material is cooled at the tip at approximately 0° C. to about −160° C.

* * * * *

UNITED STATES PATENT AND TRADEMARK OFFICE
CERTIFICATE OF CORRECTION

PATENT NO.       : 9,241,754 B2                                   Page 1 of 1
APPLICATION NO.  : 13/834619
DATED            : January 26, 2016
INVENTOR(S)      : McKay It is certified that error appears in the above-identified patent and that said Letters Patent is hereby corrected as shown below:

In the Specification

In Column 7, Line 11, delete "probes 16, 18" and insert -- prongs 16, 18 --, therefor.

In Column 7, Line 29, delete "prongs 22, 24" and insert -- tips 22, 24 --, therefor.

In Column 7, Line 39, delete "-3° C., -2° C.,-1° C.," and insert -- "-30° C., -20° C.,-10° C., --, therefor.

Signed and Sealed this
Twelfth Day of July, 2016

Michelle K. Lee
*Director of the United States Patent and Trademark Office*